March 27, 1945. W. H. OTT Plant Pat. 656

CHERIMOYA TREE

Filed Sept. 11, 1944

Inventor
W. H. Ott
By: Robbins & Robbins
attorneys.

Patented Mar. 27, 1945

Plant Pat. 656

UNITED STATES PATENT OFFICE

656

CHERIMOYA TREE

William Henry Ott, Whittier, Calif., assignor to Armstrong Nurseries, Inc., Ontario, Calif., a corporation of California Application September 11, 1944, Serial No. 553,654

1 Claim. (Cl. 47—62)

Figure 1:
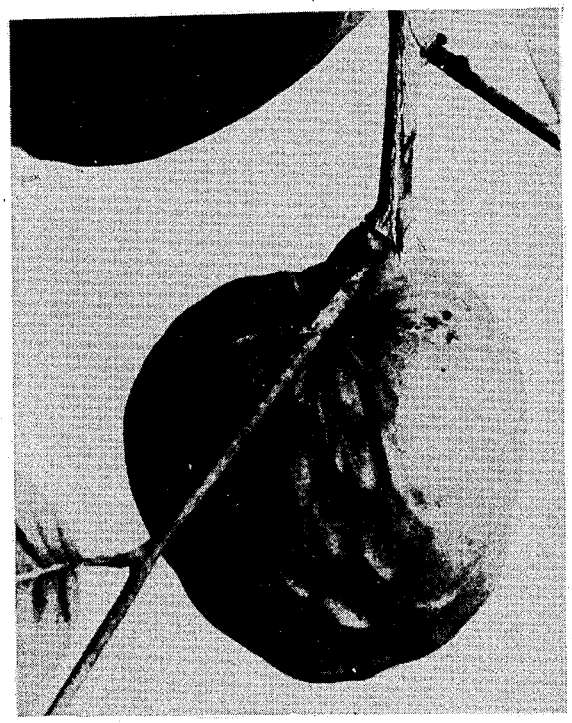

The present discovery relates to a new and distinct variety of cherimoya, a subtropical fruiting tree well known in California. This new variety originated as a seedling grown on my property at Whittier, California, the first asexual propagation fruiting in the season of 1944.

The first ripe fruit of the present variety for this year's season was picked about January 1st and the last ripe fruit was picked about May 1st. It is characterized as to novelty by many distinctions, among the more important of which may be mentioned the characteristic of the original tree of a much greater quantity of fruit produced without hand pollination over a long period of tests and a much greater uniformity and distinctiveness of flavor and eating quality throughout the entire ripening season, as compared with other existing cherimoya varieties.

In further comparison with other varieties, the present one has a uniform shape where the fruits result from open pollination and the tough and medium thick skin and its smooth surface make it a more suitable fruit for shipping and handling without injury and subsequent deterioration.

Another important characteristic is the ability of the fruit of this variety, when picked in the early part of the maturing season, to ripen and come to full flavor after the picking even when the fruit picked is very immature, as distinguished from the habit of other varieties picked at that period when immature of merely hardening and solidifying. Naturally, this is of considerable importance from a shipping standpoint.

In size, it is somewhat smaller than the fruit of such well known varieties as "Booth," "Whaley," "Dr. White" and "Sallman."

The high sugar content of the fruit tests as much as 26.51% of the dry weight and the low seed content per ounce of fruit averages 3.3 in the location of Whittier, California, where the specimens herein described were grown, and speaking with reference to fruit grown from open pollination.

Figure 2:
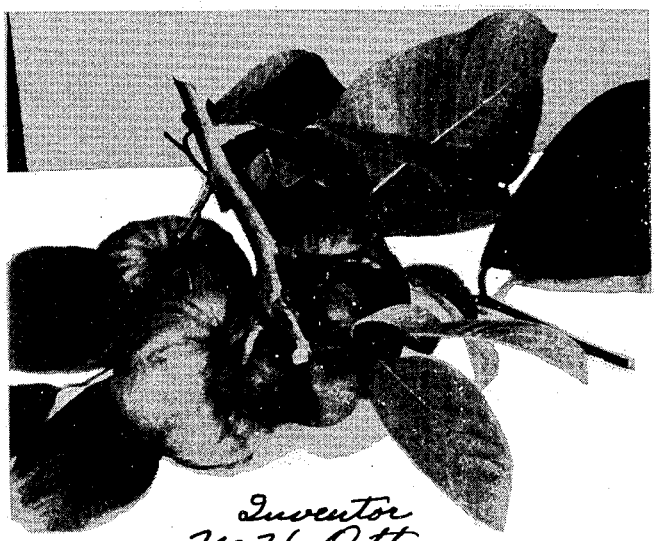

In the drawing:

Figure 1 shows a single fruit of this variety at maturity stage before picking; and Figure 2 shows a cluster of the fruit and associated foliage, directly after clipping from a branch of the tree.

Asexual reproduction of the present variety shows that the quality and general characteristics of the individual fruits above noted are shown to be stable, or fixed, by the first fruiting of progeny trees.

The following is a detailed description of this new cherimoya, the color terminology employed herein being in accord with that of the Robert F. Wilson Horticultural Colour Chart, except where obviously the meaning is the sense of the popular color term.

*Tree*

Medium size; medium vigorous; upright-spreading; open; broadly pyramidal in outline; about average in hardiness; very productive without hand pollination as is required on most varieties of cherimoyas for satisfactory production. It has borne a satisfactory crop each year since the first year that it fruited.

Trunk: Medium stocky; medium smooth.

Branches: Medium slender to slender; smooth but covered with inconspicuous tomentum; branches tend somewhat to willowiness; young, tender twigs near Sage Green (000861/2, p. 198). Tomentum of a brownish hue, undetermined, but short and quite conspicuous on youngest portions of growth. Lenticels are horizontal and vary from mere dots to one-quarter inch long. Medium in quantity and medium in size.

Leaves: Variable in length, being as much as 7 to 8½ inches on leaves borne on sucker growth and the width on the same leaves from 3¾ to 5¼ inches. Shape is typically oblong to oblong lanceolate and the apex varying from acutely tipped to rounded.

*Texture.*—Medium thin. Upper side of the mature leaf, Parsley Green (00962/1, p. 193); midrib of upper surface, Fern Green (0862/2, p. 186), without noticeable change in color toward the base. Veins with a slight variation in the color tone, Fern Green (0862, p. 186). Mature leaf, under side Willow Green (000862/1, p. 199) quite distinctly veined with a tone of Fern Green (0862/3, p. 186); system of veins abounding in a velvety pubescence on the under side but both large and small veins retaining the color tone throughout their length except very near the margin where they blend into Willow Green (000862/1, p. 199). Midrib under surface, Fern Green (0862/3, p. 186). Young leaves much the same color but more greyed in hue and covered more prominently with tomentum which is of a brownish hue.

*Petiole.*—Medium long, medium thick; color near Spinach Green (0960/3, p. 187); grooved on upper side and covered with a very fine velvety pubescence of a brownish hue. Under side, smooth but likewise pubescent.

*Flower buds.*—Medium to slightly small; medium to slightly short; outline conic pointed, heavily pubescent.

*Flowers.*—First bloom between May 1st and May 15th, varying slightly with the season. Full bloom usually about August 15th, about midseason compared with other varieties and from medium to small in size.

*Fruit*

Observed and described from February 1 to 7, 1944, as soon as soft enough to yield to firm pressure. Fruit tested, ripened under room temperatures in from five to seven days after picking.

Size: While variable, more uniform in size than most cherimoya varieties, typical fruit measuring in axial diameter, 3 to 3¼ inches, transverse diameter, 3 to 3⅜ inches, maximum diameter, 3½ to 4 inches. Weight, 7 to 12 ounces in uniformly shaped fruit, 12 ounces being approximately maximum size.

Form: Uniform while unsymmetrical, the fruits more nearly approach symmetry than do most other varieties of cherimoyas; commonly heart shaped, sometimes ovoid.

*Base.*—Usually symmetric showing shallow channeled depressions which gradually disappear as they progress toward the apex at about ⅔ of the distance from the base to the apex.

*Apex.*—Rounded, usually with faint markings and with no pistil point differentiation.

Stem: Length 1 to 1¼ inches, medium stout; heavily pubescent. Mature fruits are easily detached at a cleavage point between the stem and the branch as soon as the fruit is sufficiently mature for harvest.

*Color.*—Parallel stripes of young bark tissue approaching Sage Green (000861/1, p. 198) and more mature tissue Leek Green (000858/2, p. 197).

Skin: Medium thick, comparatively smooth, peels free of the flesh more readily than most cherimoyas and yields readily under the pressure of the thumb when ripe. No tendency to crack has been observed. Surface is finely pubescent which becomes less conspicuous at maturity. A pattern of lines much as the effect of outlines of imbricated scales are present on the surface of the skin although it is not actually scales. These scale-like appearing depressions vary in size and form, sometimes of a pentagonal or hexagonal shape with a less distinct outline toward the apex, being much more noticeable and depressed at the base. Near the base, inside the pattern of these lines there are typically depressions from which small tubercles emerge marking the location of the carpels on the inside of the fruit. Color of the skin when first ripening is near Fern Green (0862/1, p. 186) gradually changing to Fern Green (0862/2) to Fern Green (0862/3). At complete maturity it is colored with short, narrow stripes of Garnet Brown (00918/3, p. 192). They appear first along the lower border of these line patterns, and progress upward in each of the small sections. Very tiny Garnet Brown (00918/3, p. 192) spots are distributed all over the fruit at this stage. The inside skin color near Scheeles Green (860/3, p. 175).

Flesh: As observed from an axial diameter section color from skin towards center: Region near skin approximately ⅛ of an inch wide, is Barium Yellow (503/2, p. 183). Remainder of the flesh near Naples Yellow (403/1, p. 121). As the fruit ages, the central portion surrounding the removable core, or the elongation of the stem, is from Persimmon Orange (710/1, p. 91) to an undertermined brownish hue. This color shades out in the surrounding flesh to a faint Mimosa Yellow (602/3, p. 143). Surface of the seed cavity is smooth, semi-shiny. The color is Mimosa Yellow (602/3, p. 143).

*Texture.*—Very fine, semi-fibrous surrounding the seed cavity, very finely gritty close to the skin. Ripens very evenly and would be classed as equal to or superior in texture to other well known varieties.

*Flavor.*—Characteristically distinctive and delicious throughout the ripening season. A delicate and desirable sweet sub-acid taste.

*Sugar content.*—As much as 26.51% of the dry weight.

*Aroma.*—Distinct, sweet, and persistent.

*Eating Quality.*—Excellent.

Seed: Number, from 24 to 36, in a slightly slanting radial arrangement. Average seeds per ounce from open pollinated fruit varying somewhat with varied climatic conditions, but usually about 3.3.

*Size.*—Medium. Length ⅝ to ¾ inches; width ⅜ to $\frac{7}{16}$ inches.

*Form.*—Elongated, convex with two broad sides.

*Base.*—Truncate at hilum. Hilum acute pointed, slightly depressed adjacently.

*Apex.*—Rounded, sides bounded by a bordering demarcating line.

*Surface.*—Glabrous, smooth.

*Hilum.*—Concavity with definite Majolica Yellow (09, p. 102) borders. Irregular interlaced lines or stripes of Majolica Yellow (09/1, p. 102) color are often present on the dark brownish seed surface.

Use: Market and dessert.

Keeping quality: Best.

Shipping quality: Best.

General characters:

*Crop production.*—Heavy to medium.

*Bearing habit.*—Fruit both isolated and in clusters of two to five or six.

I claim:

A new and distinct variety of cherimoya tree, characterized as to novelty, in comparison with other cherimoya varieties grown under comparable conditions, by the much greater production of fruit produced without hand pollination, much greater uniformity and distinctiveness of flavor and eating quality throughout the entire ripening season, uniformity of shape of the fruit, much greater suitability for shipping due to smooth surface and toughness of skin, the habit of ripening and coming to full flavor of fruit picked before maturity during the early part of the maturing season, the high sugar content and low seed content of fruit grown from open pollination, substantially as shown and described.

WILLIAM HENRY OTT.